United States Patent
Leisner

(10) Patent No.: US 7,727,205 B2
(45) Date of Patent: Jun. 1, 2010

(54) OSTOMY DEVICE INCLUDING A COLLECTING BAG AND A BASE PLATE, AND AN OSTOMY COLLECTING BAG

(75) Inventor: Henrik Leisner, Hellerup (DK)

(73) Assignee: Coloplast A/S, Humlebaek (DE)

( * ) Notice: Subject to any disclaimer, the term of this patent is extended or adjusted under 35 U.S.C. 154(b) by 1122 days.

(21) Appl. No.: 10/532,716

(22) PCT Filed: Oct. 30, 2003

(86) PCT No.: PCT/DK03/00736

§ 371 (c)(1), (2), (4) Date: Nov. 16, 2005

(87) PCT Pub. No.: WO2004/039293

PCT Pub. Date: May 13, 2004

(65) Prior Publication Data

US 2006/0111683 A1    May 25, 2006

(30) Foreign Application Priority Data

Oct. 31, 2002   (DK) ............................... 2002 01659

(51) Int. Cl.
*A61F 5/44* (2006.01)
(52) U.S. Cl. .................. 604/342; 604/338; 604/339
(58) Field of Classification Search .......... 604/332–345
See application file for complete search history.

(56) References Cited

U.S. PATENT DOCUMENTS

| | | | |
|---|---|---|---|
| 4,367,732 A | | 1/1983 | Poulsen et al. |
| 4,867,748 A | | 9/1989 | Samuelsen |
| 4,890,608 A | * | 1/1990 | Steer ............................ 602/57 |
| 5,496,296 A | * | 3/1996 | Holmberg .................... 604/336 |
| 5,722,965 A | * | 3/1998 | Kuczynski ................... 604/344 |
| 5,776,120 A | * | 7/1998 | Shelley et al. ............... 604/339 |
| 5,800,415 A | * | 9/1998 | Olsen ......................... 604/336 |
| 5,912,059 A | | 6/1999 | Jones et al. |
| 6,764,474 B2 | * | 7/2004 | Nielsen et al. .............. 604/344 |

FOREIGN PATENT DOCUMENTS

| | | |
|---|---|---|
| EP | 0 686 381 A1 | 12/1995 |
| EP | 0 756 854 A1 | 2/1997 |
| EP | 0 793 951 A1 | 9/1997 |
| WO | WO 89/05919 | 6/1989 |
| WO | WO 96/38106 | 12/1996 |
| WO | WO 01/85074 A1 | 11/2001 |
| WO | WO 02/05735 A1 | 1/2002 |

\* cited by examiner

*Primary Examiner*—Tatyana Zalukaeva
*Assistant Examiner*—Lynne Anderson
(74) *Attorney, Agent, or Firm*—Coloplast Corp., Coloplast A/S; Daniel G. Chapik; Nicholas R. Baumann

(57) ABSTRACT

An ostomy device including a collecting bag and a base plate with an adhesive plate for being fastened on the user, the base plate having a stomal opening and a first flange for repeated and removable adhesive connection to a coupling element on the collecting bag which has a second flange. The adhesive connection is provided by at least one layer of an adhesive. Furthermore, the device includes a further flexible layer placed between the adhesive layer and the one of the first and second flanges having the lower tensile strength, the flexible layer having a yield strength exceeding the adhesive strength of the adhesive layer.

20 Claims, 1 Drawing Sheet

OSTOMY DEVICE INCLUDING A COLLECTING BAG AND A BASE PLATE, AND AN OSTOMY COLLECTING BAG

This is a nationalization of PCT/DK03/000736 filed Oct. 30, 2003 and published in English.

BACKGROUND OF THE INVENTION

1. Field of the Invention

The invention relates to an ostomy device comprising a collecting bag and a base plate with an adhesive plate for being fastened on the user, said base plate having an opening for receiving an ostomy, said base plate further comprising a first flange for repeated and removable adhesive connection to a coupling element on the collecting bag, said first flange being manufactured from a material with a first tensile strength, said coupling element comprising a second flange manufactured from a material with a second tensile strength, said adhesive connection being provided by at least one layer of an adhesive.

The invention also relates to an ostomy collecting bag comprising a coupling element that comprises a second flange for removable and adhesive connection to a first flange on a base plate and for being fastened on a user, said first flange being manufactured from a material with a first tensile strength, said second flange being manufactured from a material with a second tensile strength, said adhesive connection being provided by at least one layer of adhesive.

2. Description of the Related Art

WO 96/38106 teaches an ostomy collecting system comprising a collecting bag with an inlet opening configured in a bag wall and with surrounding connecting elements for connection to an ostomy and a carrier device for the collecting bag. The carrier device comprises a base plate for fastening on the user and has an annular first flange connected to the base plate. The connecting elements comprise a second flange, which is permanently connected to the collecting bag and is configured to constitute a removable and adhesive connection to the first flange.

WO 01/85074 also describes an ostomy collecting system. The adhesive connection between the collecting bag and the carrier device is provided by an adhesive layer being applied onto one part, whereby repeated adhesions of the two flanges are possible. Both the first and the second flange are flexible and manufactured from elastic materials.

When designing adhesive couplings for this purpose, different materials are frequently used for the two coupling parts, and an increased flexibility for the coupling system is often achieved by using a very soft material for at least one of the coupling flanges, eg a foamed material like PE or EVA foam, preferably with closed cells. The adhesive is normally designed to yield as high an adhesive force as possible while still keeping a separable connection.

However, as the long-term properties of an adhesive connection may vary due to production variations, problems are experienced when separating the adhesive connection for removing the bag or repositioning the bag on the base plate. If, due to the above-mentioned variations, the adhesive forces become higher than the tensile strength of the softer material, residues of this material and the adhesive are left on the counterpart of the coupling, thereby compromising the proper functioning of the part which would normally be re-used by incurring a risk of leakage or even involuntary disconnection of the coupling system.

It should be mentioned that the term 'elasticity' is used for the material properties. A high elasticity module is characteristic of a rigid material, while a low elasticity module is characteristic of an elastic material.

'Flexibility' expresses a property of a component of a product: its ability to be bent, and it depends on the chosen material and the dimensions of the element.

SUMMARY OF THE INVENTION

It is thus the object of the present invention to provide an ostomy device and an ostomy collecting bag that solve said problems and whereby an adhesive coupling connection is provided between bag part and body portion in such a manner that deformations and tearing out of the flange material are prevented, and whereby good coupling connection is obtained without a risk of adhesive agent residue and foam being left behind on the surface that was supposed to be clean and ready to receive a fresh, unused bag flange.

This problem is solved by an ostomy device having a collecting bag and a base plate with an adhesive plate for being fastened on the user, the base plate having an opening for receiving an ostomy and a first flange for repeated and removable adhesive connection to a coupling element on the collecting bag. The first flange is made from a material with a first tensile strength, and the coupling element includes a second flange made from a material with a second tensile strength. The adhesive connection is provided by at least one layer of an adhesive. A further flexible layer is placed between the adhesive and the flange with the lower tensile strength, this flexible layer having a yield strength exceeding the adhesive strength of the adhesive.

This problem is also solved by an ostomy collecting bag having a coupling element that includes a flange for removable and adhesive connection to another flange on a base plate for being fastened on a user. The coupling element flange is manufactured from a material with a first tensile strength, and base plate flange is manufactured from a material with a second tensile strength less than the first tensile strength, with the adhesive connection being provided by at least one layer of an adhesive. The coupling element includes a further flexible layer placed between the adhesive and the coupling element flange, the flexible layer having a yield strength exceeding the adhesive strength of the adhesive.

The terms "tensile strength" and "yield strength" are generally used to define mechanical properties of materials, incorporating plastics as in e.g. the ISO standards 527.1-4.

By the term "tensile strength" (or "ultimate tensile strength") as used herein is meant the maximum resistance in the material to fracture. By the term "yield strength" (or "tensile yield strength") as used herein is meant the maximum stress at which permanent, non-elastic deformation in the material begins.

For most plastic materials the material's tensile strength is the higher of the two and the yield strength significantly lower.

Thus the operating principles consist in that the flexible layer covers the surface of the flange manufactured from the material with the lowest tensile strength and hereby protects the material from being torn out even if its tensile strength is low. Further the modulus of elasticity for the flange will be low if it is desired to have a very soft flange.

As the flexible layer has a yield strength that exceeds the adhesive strength of the adhesive layer, it is ensured that no deformations of the flanges and the flexible layer take place during coupling and decoupling.

It is also possible that both flanges have been manufactured in a material with the same tensile strength. In that case the flexible layer covers the surface of the most flexible element.

The invention according to one embodiment operates in the following way:

A base plate is mounted on the user, and wherein the first flange of this base plate is somewhat more rigid than the flange located on the bag part as such. Preferably the first flange is manufactured from a plastics material that is elastic, but possesses—as mentioned—a higher degree of rigidity but still provides a flexible product.

The flange of the bag part, designated the second flange, is also made of an elastically deformable material, e.g. the foam material as such being a preferred embodiment. The second flange is more flexible than the first flange. The tensile strength of the material of the second flange is smaller than the tensile strength of the material of the first flange. Onto this foam material, a further flexible layer, a foil or a film, is applied and it can be applied in various ways, e.g. in the form of a double-coated adhesive film, whereby the layer is caused to sealingly adjoin the subjacent foam. On the opposite face it has a further adhesive connection and is provided with a layer of adhesive that enables it to adhere to the surface of the first flange. This adhesive layer might also be placed on the surface on the first flange.

Precisely by providing such intermediate layer between the foam material that has the lowest tensile strength and the rather more rigid flange of the body portion and with the highest tensile strength, it is ensured that the foam material is not torn out when an adjustment of the coupling connection occurs; this intermediate layer having a yield strength that exceeds the adhesive strength provided in the adhesive coupling as such. It is ensured that the subjacent foam flange may still have its good, flexible and elastic properties intact, whereby the user still obtains very good and sealing adhesive coupling connection without a risk of seepage. In this embodiment the flange of the body portion is rather more rigid than the flange portion of the bag as such, since the rather more rigid flange of the body portion has to be able to absorb the forces and the ensuing deformations that may occur as a consequence of the movements of the user. The flange of the collecting bag possesses a larger elasticity and a larger flexibility than this rather rigid part, and this part of the adhesive coupling ensures a sealing connection to the first flange, since the soft portion is capable of accurately following the surface and, likewise, it is capable of following bending, if any, should that occur. The combination with a somewhat more rigid flange on the body portion and a more soft, elastic and flexible part on the other flange and wherein this new layer has been inserted thus serves to conserve the high degree of user-friendliness, while simultaneously it serves to prevent tearing off of the subjacent foam material.

It is further obtained that it is possible, too, to remove and remount one or more bags without the longevity of the base plate being reduced, while simultaneously it is avoided to have to spend time performing a cleaning of the base plate when the collecting bag is being replaced, and at the same time to eliminate the risk of tearing, since the variations that may occur in the cohesive power of the foam is thus not allowed to influence the coupling in any way; the further second flexible layer constituting a kind of barrier that serves, for one thing, to keep the foam material as such together and, for another, to act as the adhesive portion that is to engage with the surface of the first flange. The flexible layer has an area expanse that corresponds to the entire area expanse of the adhesive connection In another embodiment it is also possible that the flexible film is placed on and covers the surface of the first flange. This is the case when the first flange has been manufactured from a material with a lower tensile strength compared to the material of the second flange.

Further it should be noted that the layer of adhesive might be placed on the surface of the flexible layer and facing towards the flange with which it engages, or it may be placed on the engaging surface as such. Finally it is possible to place an adhesive layer on both surfaces.

By providing an ostomy device and an ostomy collecting bag in accordance with the invention and as further featured in claim 2, it is obtained that the flexible layer adjoins the subjacent layer so closely that it is not torn off during removal of the bag.

By providing an ostomy device and an ostomy collecting bag in accordance with the invention and as further featured in claim 3, it is obtained that the flexible layer is not deformed when engaging with the flange with the highest tensile strength.

By providing an ostomy device and an ostomy collecting bag in accordance with the invention and as further featured in claim 4 it is possible to obtain a soft flange and a product that are pleasant for the user to wear.

By providing an ostomy device and an ostomy collecting bag in accordance with the invention and as further featured in claim 5, a convenient configuration of the adhesive coupling is provided, which is of particular interest in case precisely a first flange is used that is made of a plastics material and exhibits a higher degree of rigidity than the second flange, and where the second flange is preferably made of a foam material.

However, a higher degree of rigidity and flexibility can be obtained in various ways, eg by manufacture thereof from the same material as the second flange, but in a thicker layer.

When an ostomy device and an ostomy collecting bag are provided in accordance with the invention and as further featured in claim 6, a convenient way is obtained in which it is possible to establish the flexible layer and the adhesive layer.

When an ostomy device and an ostomy collecting bag are provided in accordance with the invention and as further featured in claims 7-8, a convenient choice of material is obtained for the flanges.

Finally, the invention relates to use of the ostomy collecting bag for an ostomy device and as is featured in claim 10.

BRIEF DESCRIPTION OF THE DRAWING

The invention will now be explained in further detail with reference to the drawing, wherein.

DETAILED DESCRIPTION OF THE PREFERRED EMBODIMENTS

Figure 1:
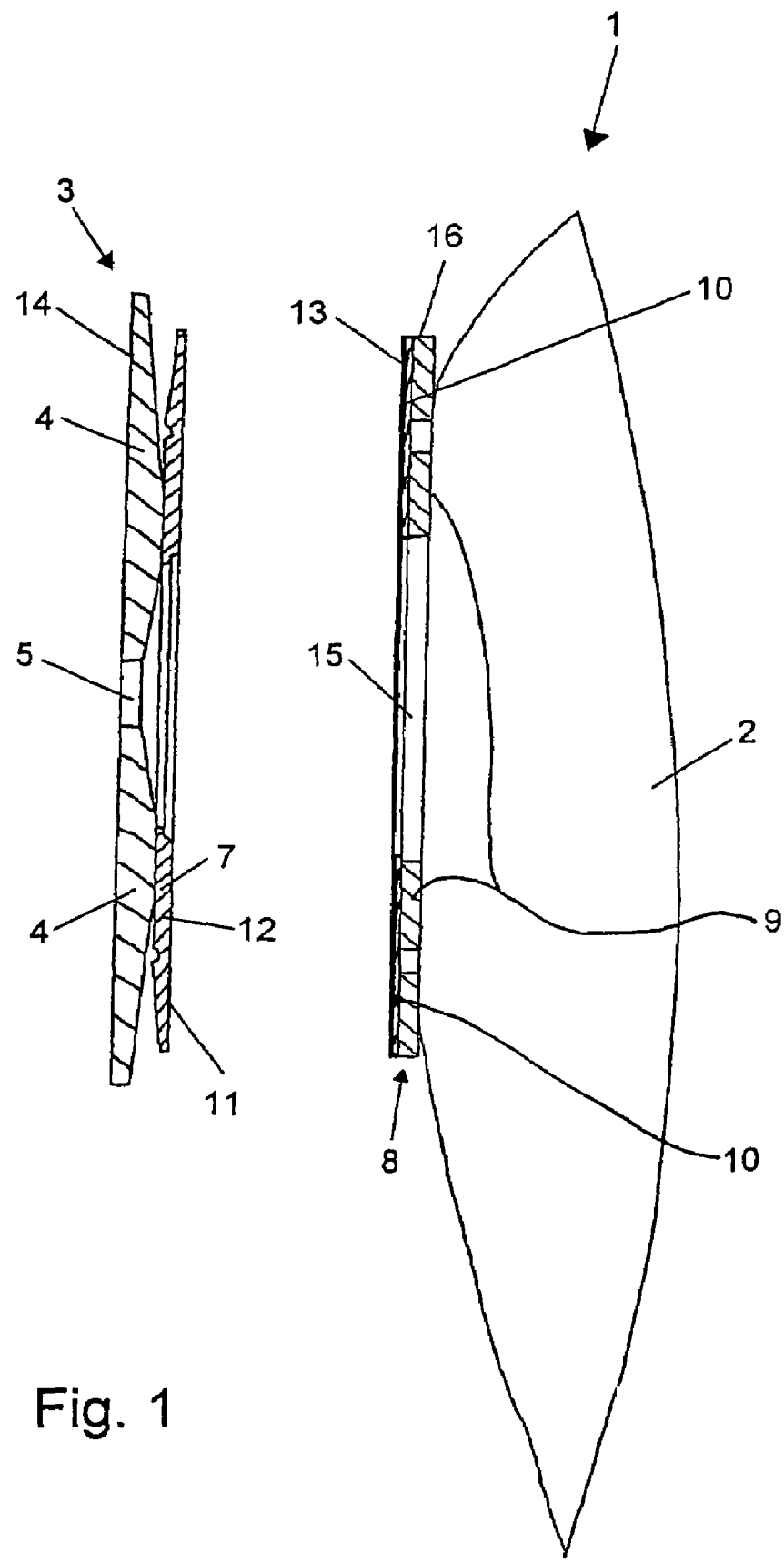
FIG. 1 is a sectional view of one embodiment of an ostomy device according to the invention and comprising a collecting bag and a base plate.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

FIG. 1 shows an ostomy device 1 comprising a base plate 3 and an ostomy collecting bag 2, respectively. The collecting bag 2 collects faeces, and a second flange 9 for fastening the bag 2 around the same opening in the form of an ostomy in the abdominal wall of the user is mounted thereon. In the wall of the collecting bag, an inlet opening 15 is provided through which faeces may enter. The collecting bag 2 can be closed or open able at the bottom for occasional discharge of its contents. Between the second flange 9 and the outer wall of the bag, connecting elements are provided, whereby a reliable connection between the two elements is obtained. This may be accomplished by means of a welding, a gluing or in some other manner. The opening 15 is provided such that that it extends through both the bag wall and through the flange. Typically the diameter will be within the range of 6-10 cm, preferably between 7 and 9 cm. The base plate 3 as such comprises an adhesive plate 4 that is, by means of an adhesive agent 14 applied onto its rear side, configured for adhering to the user's skin. Typically adhesives of this kind are mentioned in U.S. Pat. No. 4,367,732, U.S. Pat. No. 4,867,748 and WO 89/05619. The skin plate or the adhesive plate 4 carries a first flange 7 and in this annular flange as well as within the adhesive plate as such an opening 5 is provided, through which an ostomy extends.

The tensile strength of the material of the second flange 9—and the mentioned second tensile strength—is lower than the tensile strength—and the mentioned first tensile strength—of the first flange 7.

Typically it is possible to carry out an adjustment of the diameter of the opening from about 5 mm and up to 70 mm, whereby, by cutting, it is possible to vary the size of the opening for the ostomy. The first flange 7 is attached to the adhesive plate 4, e.g. by means of an adhesive agent or by means of weldings and the like. The rim part of the first connecting section 7 typically has, at its periphery, a freely movable flange area, which is thus movable in relation to the adhesive plate 4 as such, whereby it is ensured that the adhesive coupling, as will be described below, is caused to operate optimally. It is further noted that there may be differences in the rigidity of the first flange, whereby the first connecting section comprises a rim section 11 and which is movable in relation to the base plate and exhibits a higher degree of flexibility than the inner portion 12 of the flange. This difference in flexibility can be provided either by differences in choice of material or by different ratios in thickness between the two parts.

The first flange can be cast in a water-repellent foam material, such as ethyl vinyl acetate EVA or polyurethane PU with closed cells, thereby avoiding that the foam plastics material absorbs liquid. However, it is preferably preferred to manufacture this first flange 7 from a plastics material, typically polyethylene, and polypropylene and modified with EVA. However, it is expedient, no matter what material is selected, that the rigidity of this first flange 7 exceeds the rigidity of the second flange 9 and that the second flange is typically manufactured from said foam plastics material. In principle, the two flanges may be manufactured from the same material, but the first flange is not manufactured from a foam material.

Preferable the modulus of elasticity of the material of the first flange 7 exceeds the modulus of elasticity of the second flange 9.

The collecting bag 1 as such comprises a coupling element 8, which coupling element 8 comprises a second flange 9; as mentioned manufactured from a foam material. On the surface of the foam material and facing towards the first flange 7, a film is arranged, a so-called further flexible layer 10, and wherein this film is typically manufactured from PE, PP, polyester. The film will have a thickness of 50-500 μm depending on the selected material and will cover the entire face to adjoin the first flange for providing a coupling connection. Thus the film 10 forms part of the coupling element 8.

On the outer face of the film that faces towards the first flange, an adhesive 13 is arranged in the form of a thin washable adhesive agent that may be e.g. a hydrogel adhesive or an acrylate adhesive or an adhesive of the hot melt type. The adhesive agent is applied in a thin layer, on the one hand for keeping the thickness small and on the other for maintaining the flexibility and elasticity of the film. Application of the adhesive may be accomplished by coating, spraying or application in a suitable pattern. Besides, the adhesive surface, the one creating the adhesive coupling, is covered by an adhesive-repellent coating.

The connection of the flexible layer 10 to the subjacent second flange may be provided optionally by adhesion or by means of welding. Optionally the flexible layer may be provided by a caching process or the flexible layer can be provided by means of a spraying or coating, and application of the adhesive agent is subsequently to take pace. However, it is imperative that the adherence between said flexible layer 10 and the subjacent, flexible second flange is of such nature that the adherence exceeds the adherence of the adhesive coupling connection that occurs between the surface of the first flange and the adhesive agent applied onto the flexible layer 10.

As mentioned, the varying nature of rigidities can be obtained either by using the same material for the two flanges, but wherein a thicker material is used specifically for the basis plate flange, or another material may be used, eg a plastics material with a elasticity module that exceeds that of the foam material used on the bag coupling portion as such.

In order to ensure that the flexibility of the bag part is maintained despite the application of said film, it should be mentioned in this context that the film covers exclusively the face that faces towards the base plate and its first flange. Thus, it is not the case that the second flange 9 of the bag part is wrapped in a flexible layer on all its faces and subsequently mounted on the bag, but rather that it is essentially the plane face facing towards the base plate that is covered by said film. Optionally the film may also seize around the annularly extending sides 16 of the second flange, if convenient in connection with the manufacture thereof. Further the connecting strength between the flexible layer 10 and the flange with the material with the lowest tensile strength—the second flange 9—exceeds the adhesive strength of the adhesive.

Flexibility in this context is to be understood such that the flanges are pliable and possess a given elasticity. The difference in the elasticity and flexibility of the first flange and the second flange can be established by the module of elasticity of the first flange substantially exceeding the module of elasticity of the second flange. Likewise, it is imperative that the yield strength of the flexible layer 10 exceeds the adhesive strength of the adhesive connection provided by an adhesive layer 13 placed between the first flange 7 and the coupling element 8, and likewise it exceeds the yield strength of the second flange. The yield strength of the flexible layer 10 is in the same order of magnitude as the yield strength of the flange having the largest tensile strength.

The adhesive layer is in this example placed on the flexible layer, but could be placed on the first flange or on both surfaces. Further the first flange 7 is manufactured from an elastic material and has a tensile strength that is larger than the tensile strength of the material of the second flange 9 and the modulus of elasticity of the material of the first flange 7 exceeds the modulus of elasticity of the material of the second flange 9.

Further, the tensile strength of the flexible layer exceeds or is in the same order of magnitude as the tensile strength of the second flange 7.

The variations in the cohesive force of the foam in the second flange do not influence the durability of the coupling connection, since this foam material is thus covered by said flexible film 10, and thus it is exclusively this film that will absorb the tensile and pressure forces that may occur during mounting/dismounting of the bag part in relation to the base plate.

Further the modulus of elasticity of the flexible layer 10 is substantially larger than the modulus of elasticity of the material of the second flange 9 as this flange has the lowest tensile strength.

It is noted that this intermediate layer of film imparts to this coupling element a resistance to deformations in the plane of the element without significantly modifying the bending properties. The first flange and second flange, may be of different size, but thus such that the adhesive portion does not extend beyond the counterpart. Preferably the adhesive portion of the adhesive coupling is perceived to be provided on the flange of the bag part and on top of the flexible layer 10, but it is possible, however, to perform an application of said adhesive film on the flange of the base plate as such, in particular in those cases where it is manufactured from a foam material, and wherein the foam material has a thickness that exceeds that of the flange on the bag for providing increased rigidity. Optionally the increased rigidity may also be accomplished by selection of a foam material that inherently possesses a larger rigidity compared to the foam material seen on the bag part. Finally, it is an option that the free surfaces of both flanges are adhesive.

However, it is essential to this embodiment that the flange of the bag part is manufactured from a foam material of a closed nature.

In a preferred embodiment, the bag coupling flange or second flange 9 is cut directly from a laminate supplied by Avery Dennison Corp. consisting of 1 mm PE foam, a layer of acrylate adhesive, a foil of especially modified PE (EMA), another layer of acrylate adhesive and a siliconized paper release liner. The foam side is fixed to the bag in a manner known per se and the release liner is removed immediately prior to use.

It should further be mentioned that it is an option to apply both the first and the second flanges with outwardly protruding tabs that facilitate removal of the bag and removal and adjustment, respectively, of the base plate.

For the protection of the adhesive it may be covered by a protection layer, eg a siliconized paper material, which is removed before use of the coupling. When using the ostomy device for the invention, the base plate is thus located on the user, the skin plate being located against the skin and the ostomy being extended through the hole. The release liner of the collecting bag is removed to expose the layer of adhesive agent, when the latter is located on the flexible film on top of the face of the second flange as such. Subsequently the second flange is adhered to the first plate around the ostomy.

In a second embodiment of the invention, the flexible layer is placed on the first flange of the base plate, this flange now having the material properties defined in the first embodiment for the second flange. Further the second flange now has the material properties defined in the first embodiment for the first flange.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. An ostomy device comprising:
   a body side member with an adhesive plate for being fastened on the user, said body side member having an opening for receiving an ostomy and a first flange manufactured from a material with a first tensile strength;
   a collecting bag including a coupling element having a second flange manufactured from a material with a second tensile strength, said first flange being configured for repeated and removable adhesive connection to said coupling element; and
   a flexible layer bonded to an outer surface of said second flange and an adhesive layer affixed to said flexible layer so that said flexible layer is sandwiched between the adhesive layer and the second flange, said bond between the outer surface of the second flange and the flexible layer being stronger than a connection between the first flange and the adhesive layer of said collecting bag coupling element,
   said flexible layer having a yield strength exceeding an adhesive strength of the adhesive layer.

2. The ostomy device according to claim 1, wherein the yield strength of the flexible layer is in a same order of magnitude as a yield strength of the first flange.

3. The ostomy device according to claim 1, wherein a modulus of elasticity of the flexible layer is substantially larger than a modulus of elasticity of the second flange.

4. The ostomy device according to claim 1 wherein the flexible layer includes a double-coated adhesive film.

5. The ostomy device according to claim 1 wherein the tensile strength of the first flange is larger than the tensile strength of the second flange, the second flange including a closed foam material.

6. The ostomy device according to claim 1 wherein a modulus of elasticity of the material of the first flange exceeds a modulus of elasticity of the material of the second flange.

7. The ostomy device according to claim 1 wherein the second flange includes a foam material and the flexible layer is a film made of at least one of polyethylene, polypropylene or polyester.

8. The ostomy device according to claim 1 wherein the flexible layer includes a film that is bonded to the second flange by welding or adhesion.

9. An ostomy collecting bag for use with a separate base plate adhered to the skin of a user, the ostomy collecting bag comprising: a coupling element having a flange for removable and adhesive connection to another flange on the base plate, a flexible layer bonded to an outer surface of said coupling element flange, and an adhesive layer affixed to said flexible layer so that said flexible layer is sandwiched between the adhesive layer and the coupling element flange, said flexible layer having a yield strength exceeding an adhesive strength of the adhesive layer, and a strength of the bond between said flexible layer and said coupling element flange also exceeding the adhesive strength of said adhesive layer.

10. The ostomy collecting bag according to claim 9, wherein a modulus of elasticity of the flexible layer is larger than a modulus of elasticity of the material of the coupling element flange.

11. The ostomy collecting bag according to claim 9 wherein the flexible layer includes a double-coated adhesive film.

12. An ostomy device comprising:
- a base plate with an adhesive plate for being fastened on the user, said base plate having an opening for receiving an ostomy and a first flange manufactured from a material with a first tensile strength;
- a collecting bag including a coupling element having a second flange manufactured from a material with a second tensile strength lower than said first tensile strength, said first flange being configured for repeated and removable adhesive connection to said coupling element;
- a flexible layer bonded to an outer surface of said second flange; and
- a layer of adhesive affixed to an outer surface of said flexible layer and having an adhesive strength to provide said adhesive connection between said first flange and said coupling element, said flexible layer having a yield strength exceeding the adhesive strength of the adhesive layer.

13. The ostomy device according to claim 12, wherein a connecting strength of the bond between the flexible layer and the second flange exceeds the adhesive strength of the adhesive.

14. The ostomy device according to claim 12, wherein the yield strength of the flexible layer is in a same order of magnitude as a yield strength of the first flange.

15. The ostomy device according to claim 12, wherein a modulus of elasticity of the flexible layer is substantially larger than a modulus of elasticity of the material of the second flange.

16. The ostomy device according to claim 12, wherein the flexible layer includes a double-coated adhesive film.

17. The ostomy device according to claim 16, wherein the film is bonded to the second flange by welding or adhesion.

18. The ostomy device according to claim 12, wherein the flexible layer is a film provided by means of a spraying or coating on the second flange and has a thickness of about 50-500 µm.

19. The ostomy device according to claim 12 wherein the second flange includes a foam material.

20. The ostomy device according to claim 12 wherein the flexible layer is a film made of at least one of polyethylene, polypropylene or polyester, and the second flange includes a foam material.

* * * * *